(12) United States Patent
Phillips et al.

(10) Patent No.: US 6,291,513 B1
(45) Date of Patent: Sep. 18, 2001

(54) FUNGICIDAL COMPOSITIONS AND METHODS OF MAKING THEREOF

(75) Inventors: Wendell G. Phillips, Wildwood; Michael K. Mao; Chun Ma, both of Chesterfield; Thomas L. Fevig, Wildwood, all of MO (US)

(73) Assignee: Monsanto company, St. Louis, MO (US)

( * ) Notice: Subject to any disclaimer, the term of this patent is extended or adjusted under 35 U.S.C. 154(b) by 0 days.

(21) Appl. No.: 09/609,211

(22) Filed: Jul. 5, 2000

Related U.S. Application Data

(62) Division of application No. 09/326,225, filed on Jun. 4, 1999, now Pat. No. 6,140,511.
(60) Provisional application No. 60/088,398, filed on Jun. 5, 1998.

(51) Int. Cl.[7] .......................... A01N 43/06; A01N 43/08; A01N 43/36
(52) U.S. Cl. ..................... 514/444; 514/471; 514/473; 514/423; 514/424; 548/406; 548/452; 548/537; 549/4; 549/52; 549/55; 549/62; 549/214; 549/434; 549/450
(58) Field of Search ..................... 514/444, 471, 514/473, 423, 424; 548/406, 452, 537; 549/4, 52, 55, 62, 214, 434, 450

(56) References Cited

U.S. PATENT DOCUMENTS 5,486,621   1/1996   Phillion et al. .

FOREIGN PATENT DOCUMENTS

| 0 538 231 A1 | 5/1993 | (EP) . |
| WO 93/07751 | 4/1993 | (WO) .............. A01N/55/00 |

OTHER PUBLICATIONS

Kim, Sunggak, et al., "Intramolecular Insertion Reaction Of Alkylidenecarbenes Into Oxygen–Silicon Bonds," *Tetrahedron Letters*, vol. 36, No. 27, pp. 4845–4848 (1995).

*Primary Examiner*—Amelia Owens
(74) *Attorney, Agent, or Firm*—Thomas P. McBride; Howrey Simon Arnold & White, LLP

(57) ABSTRACT

The fungicidal compound 4,5-dimethyl-N-2-propenyl-2-(trimethylsilyl)-3-thiophenecarboxamide (Formula (I)) has shown superior and unexpected control of the growth of the soil-borne fungus *Gaeumannomyces graminis* (*Gg*). The present invention provides a novel compound for synthesizing the compound of Formula (I) which uses the compound 4-hydroxy-4,5-dimethyl-2-trimethylsilanyl-dihydrothiophene-3-carboxylic acid allylamide (Formula (II)) as well as novel compounds of synthesizing the allylamide. In addition, Formula (II) itself has unexpectedly been found to provide control of *Gg*. Therefore, the compounds having Formula (III):

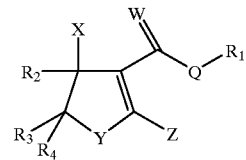

(III)

or an agronomic salts and compositions thereof are expected to provide such control as well; wherein:

Q is —NH, S, or O;

W is O, or S;

X is —OH, —OAc, —OR, where R is lower alkyl;

Y is S, O, or —NH;

Z is —Si(R)$_3$, —C(R)$_3$, where R is lower alkyl;

$R_1$ is a lower alkyl, allyl, or propargyl;

$R_2$ is a lower alkyl or aryl; and $R_3$ and $R_4$ are independently chosen from hydrogen, a lower alkyl and aryl;

optionally, $R_2$ and $R_3$ together form a 5- or 6-membered ring.

88 Claims, No Drawings

FUNGICIDAL COMPOSITIONS AND METHODS OF MAKING THEREOF

This is a Division Ser. No. 9/326,225 filed Jun. 4, 1999 now U.S. Pat. No. 6,140,511.

This is a conventional application based on U.S. patent application Ser. No. 60/088,398, filed Jun. 5, 1998.

FIELD OF THE INVENTION

This invention relates to certain novel substituted heterocyclic compounds, methods for synthesizing novel substituted heterocyclic compounds, a method for the control of Take-All disease in plants, particularly cereals, by the use of the compounds, and fungicidal compositions for controlling Take-All disease.

BACKGROUND OF THE INVENTION

Take-All disease is a serious problem in the production of cereals, particularly wheat and barley. It is caused by the soil-borne fungus *Gaeumannomyces graminis* (*Gg*). The fungus infects the roots of the plant, and grows throughout the root tissue, causing a black rot. The growth of the fungus in the roots and lower stems prevents the plant from obtaining sufficient water and/or nutrients from the soil, and is manifested as poor plant vigor and, in severe instances of disease, by the formation of "whiteheads," which are barren or contain few, shriveled grains. Yield loss results. Gaeumannomyces species also infect other cereal crops, for example, rice and oats; and turf.

Currently the primary means of avoiding crop loss due to infestation of the soil by *Gg* has been to rotate the crop grown to one which is resistant *Gg*. However, in areas where the primary crops are cereals, rotation is not a desirable practice, and an effective control agent is greatly desired.

U.S. Pat. No. 5,486,621, hereby incorporated by reference, discloses a unique fungicidal composition, 4,5-dimethyl-N-2-propenyl-2-(trimethylsilyl)-3-thiophenecarboxamide, which provides superior and unexpected control of Take-All disease. It is an object of this invention to provide novel methods for synthesizing this unique fungicide. In addition, International Application No. PCT/US92/08633 discloses a broad scope of compounds effective against Take-All disease. Objects of the present invention also include providing additional novel compounds which will control the growth of *Gg* in the soil to reduce crop loss and providing novel methods for preparing such compounds. Further objects of this invention include providing an effective method for control of Take-All disease in plants and fungicidal compositions that may be used for control of Take-All disease as a seed treatment or as a soil treatment.

These and other objects of the invention will be apparent to those skilled in this art from the following description of the invention.

SUMMARY OF THE INVENTION

The fungicidal compound 4,5-dimethyl-N-2-propenyl-2-(trimethylsilyl)-3-thiophenecarboxamide, claimed in U.S. Pat. No. 5,486,621, Formula (I):

has shown superior and unexpected control of the growth of the soil-borne fungus *Gaeumannomyces graminis* (*Gg*). The present invention provides a novel method for synthesizing this fungicidal compound which uses the compound 4-hydroxy4,5-dimethyl-2-trimethylsilanyl-dihydrothiophene-3-carboxylic acid allylamide, Formula (II):

In addition, the compound of Formula (II) has unexpectedly been found to provide control of Take-All disease. Therefore, the compounds of Formula (D) are expected to provide such control as well. The structure of Formula (III) is:

or an agronomic salt thereof; wherein:
Q is —NH, S, or O;
W is O, or S;
X is —OH, —OAc, —OR, where R is lower alkyl;
Y is S, O, or —NH;
Z is —Si(R)$_3$, —C(R)$_3$, where R is lower alkyl;
R$_1$ is a lower alkyl, allyl, or propargyl;
R$_2$ is a lower alkyl or aryl; and
R$_3$ and R4 are independently chosen from hydrogen, a lower alkyl and aryl;
optionally, R$_2$ and R$_3$ together form a 5- or 6-membered ring.

As used herein, the term "alkyl," unless otherwise indicated, means an alkyl radical, straight or branched chain, having, unless otherwise indicated, from 1 to 10 carbon atoms.

As used herein, the term "aryl," unless otherwise indicated, means a phenyl substituted with alkyl, alkoxy, halogen, nitro or cyano.

The invention also provides methods for using and for synthesizing the fungicidal compound of Formulas (I)–(III), methods for controlling *Gg* comprising applying a fungicidally effective amount of the compound of Formulas (I)–(III), and fungicidal compositions for use in controlling *Gg*.

DESCRIPTION OF ILLUSTRATIVE EMBODIMENTS

Control of *Gg* diseases, including Take-All, using a chemical control agent may be accomplished in several ways. The agent may be applied directly to soil invested with *Gg*, for example, at the time of planting along with the seed. Alternatively, it may applied after planting and germination. Compositions for soil application include clay granules which may be applied in-furrow, as broadcast granules or as impregnated fertilizer granules. In addition, the agent may be applied to the soil as a preemergent or postemergent spray. Preferably, however, it is applied to the seed in a coating prior to planting. This technique is commonly used in may crops to provide fungicides for control of various phytopathological fungi.

Compositions of the present invention may comprise a fungicidally effective amount of one or more of the compounds described above and one or more adjuvants. The active ingredient may be present in such compositions at levels from about 0.01 to about 95 percent by weight. Other fungicides may also be included to provide a broader spectrum of fungal control or to enhance the control of Take-All disease provided by the compounds of the present invention. The choice of fungicides will depend on the crop and the diseases known to be a threat to that crop in the location of interest.

The fungicidal compositions of this invention, including concentrates which require dilution prior to application, may contain at least one active ingredient and an adjuvant in liquid or solid form. The compositions may be prepared by admixing the active ingredient with an adjuvant including diluents, extenders, agronomically acceptable carriers, and conditioning agents to provide compositions in the form of finely-divided particulate solids, granules, pellets, solutions, dispersions or emulsions. Thus, it is believed that the active ingredient could be used with an adjuvant such as a finely-divided solid, a liquid of organic origin, water, a wetting agent, a dispersing agent, an emulsifying agent or any suitable combination of these.

Suitable wetting agents are believed to include alkyl benzene and alkyl naphthalene sulfonates, sulfated fatty alcohols, amines or acid amides, long chain acid esters of sodium isothionate, esters of sodium sulfosuccinate, sulfated or sulfonated fatty acid esters, petroleum sulfonates, sulfonated vegetable oils, ditertiary acetylenic glycols, polyoxyethylene derivatives of alkylphenols (particularly isooctylphenol and nonylphenol) and polyoxyethylene derivatives of the mono-higher fatty acid esters of hexitol anhydrides (e.g., sorbitan). Preferred dispersants are methyl cellulose, polyvinyl alcohol, sodium lignin sulfonates, polymeric alkyl naphthalene sulfonates, sodium naphthalene sulfonate, polymethylene bisnaphthalene sulfonate and neutralized polyoxyethylated derivatives or ring-substituted alkyl phenol phosphates. Stabilizers may also be used to produce stable emulsions, such as magnesium aluminum silicate and xanthan gum.

Other formulations may include dust concentrates comprising from about 0.1 to about 60% by weight of the active ingredient on a suitable extender, optionally including other adjuvants to improve handling properties, e.g., graphite. These dusts may be diluted for application at concentrations within the range of from about 0.1 to about 10% by weight.

Concentrates may also be aqueous emulsions, prepared by stirring a nonaqueous solution of a water-insoluble active ingredient and an emulsification agent with water until uniform and then homogenizing to give stable emulsion of very finely-divided particles. Or they may be aqueous suspensions, prepared by milling a mixture of a water-insoluble active ingredient and wetting agents to give a suspension, characterized by its extremely small particle size, so that when diluted, coverage is very uniform. It is believed suitable concentrations of these formulations contain from about 0.1 to about 60% preferably about 5 to about 50% by weight of active ingredient.

Concentrates may be solutions of active ingredient in suitable solvents together with a surface active agent. Suitable solvents for the active ingredients of this invention for use in seed treatment include propylene glycol, furfuryl alcohol, other alcohols or glycols, and other solvents which do not substantially interfere with seed germination. If the active ingredient is to be applied to the soil, then solvents such as N,N-dimethylformamide, dimethylsulfoxide, N-methylpyrrolidone, hydrocarbons, and water-immiscible ethers, esters, or ketones are useful.

The concentrate compositions herein generally contain from about 1.0 to about 95 parts (preferably about 5 to about 60 parts) active ingredient, about 0.25 to about 50 parts (preferably about 1 to about 25 parts) surface active agent and where required about 4 to about 94 parts solvent, all parts being by weight based on the total weight of the concentrate.

For application to the soil at the time of planting, a granular formulation may be used. Granules are physically stable particulate compositions comprising at least one active ingredient adhered to or distributed through a basic matrix of an inert, finely-divided particulate extender. In order to aid leaching of the active ingredient from the particulate, a surface active agent such as those listed hereinbefore, or for example, propylene glycol, can be present in the composition. Natural clays, pyrophyllites, illite, and vermiculite are examples of operable classes of particulate mineral extenders. The preferred extenders are the porous, absorptive, preformed particles such as preformed and screened particulate attapulgite or heat expanded, particulate vermiculite and the finely-divided clays such as kaolin clays, hydrated attapulgite or bentonitic clays. These extenders are sprayed or blended with the active ingredient to form the fungicidal granules.

The granular compositions of the invention may contain from about 0.1 to about 30 parts by weight of active ingredient per 100 parts by weight of clay and 0 to about 5 parts by weight of surface active agent per 100 parts by weight of particulate clay.

The method of use of the fungicidal compound of the present invention may be carried out by mixing a composition comprising the active ingredient into the seed prior to planting at rates from about 0.01 to about 50 g per kg of seed, preferably from about 0.1 to about 5 g per kg, and more preferably from about 0.2 to about 2 g per kg. If application to the soil is desired, the compounds may be applied at rates of from about 10 to about 1000 g per hectare, preferably from about 50 to about 500 g per hectare. The higher application rates will be needed for situations of light soils or greater rainfall or both.

The compound 4,5-dimethyl-N-2-propenyl-2-(trimethylsilyl)-3-thiophenecarboxamide, (Formula I) may be efficiently synthesized by dehydrating4-hydroxy-4,5-dimethyl-2-trimethylsilanyl-dihydrothiophene-3-carboxylic acid allylamide (Formula (II)). The dehydration may be carried out using a weak acid such as oxalic acid or a mild dehydrating agent such as acetic anhydride in solvents such as dimethoxyethane or toluene, or by simply heating the compound of Formula (II) in a high boiling, inert solvent such as xylene. The generic compound, Formula (III), may be prepared by reacting α-mercapto-, α-hydroxy-, a α-amino ketones (which can be prepared by literature methods or by those skilled in the art) with appropriate acetylenic amides or esters in the presence of base. Preferred bases include aliphatic secondary or tertiary amines or alkali metal alkoxides. Preferred solvents include ethereal solvents such as diethoxymethane or t-butylmethyl ether, or aromatic solvents such as toluene.

The acetylenic amides and esters in turn may be prepared by several different methods. For example, reaction of appropriate and readily available acetylenes with strong bases such as n-butyl lithium or lithium diisopropylamide will generate a lithium acetylide which will react with appropriate isocyanates to produce the amides. Alternatively, silylacetylenes may react with isocyanates in the presence of acid catalysts such as aluminum chloride or methanesulfonic acid to give the amides. Substitution of the isocyanates with the corresponding chloroformates will give the corresponding esters.

Other compounds of the invention (i.e., W=S; X=Oac or OR) may be prepared from the cyclization product by methods known to those skilled in the art.

Examples of methods by which the fungicidal compound of Formula (II), 4-hydroxy-4,5-dimethyl-2-trimethylsilanyl-dihydrothiophene-3-carboxylic acid allylamide, may be synthesized are as follows:

SYNTHETIC METHOD 1

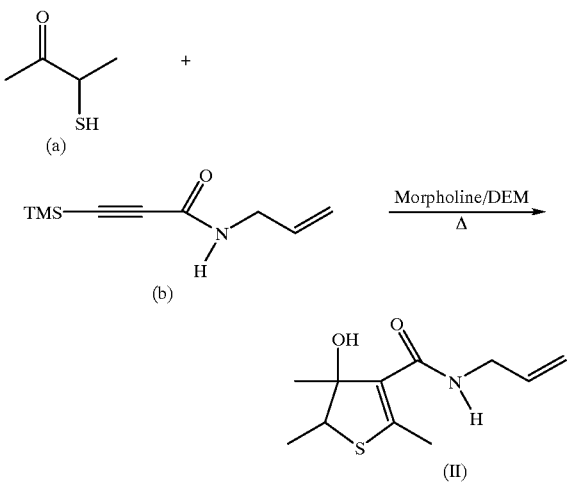

wherein morpholine is the base and DEM (diethoxymethane) is the solvent. A solution of 3-mercapto-2-butanone (a) and a base is heated to reflux and treated with N-allyl-3-trimethylsilylpropiolic amide (b). Examples of bases which may be used are sodium hydride, an aliphatic, cyclic or aromatic amine, or an alkali metal alkoxide. Examples of aliphatic amine bases are triethylamine, 1,4-diazabicyclo[2.2.2]octane (DABCO) or 1,8-diazabicyclo [5.4.0]undec-7-ene (DBU); examples of cyclic secondary amines are pyrrolidine and morpholine; and an example of an aromatic amine is pyridine. Preferred solvents include protic solvents such as water and methanol; aromatics such as toluene and chlorobenzene; aliphatics such as heptane; and ethereals such as tetrahydrofuran, diethoxymethane, t-butylmethyl ether; and dimethylsulfoxide (DMSO). The most preferred solvent is diethoxymethane. The mixture is heated at from about 60 to about 100° C. under a nitrogen atmosphere. Additional portions of the 3-mercapto-2-butanone are added, and heating is continued until the propiolic amide is consumed. The mixture is cooled and evaporated under reduced pressure. The residue is extracted into hot heptane, filtered, and the resulting solution is allowed to cool (ice/salt bath). The resulting solid precipitate is collected by filtration and dried to give 4-hydroxy-4,5-dimethyl-2-trimethylsilanyl-dihydrothiophene-3-carboxylic acid allylamide. Examples of alkali metal alkoxides are sodium methoxide, sodium tert-butoxide, and sodium tert-amylate. A preferred base is sodium tert-amylate; the most preferred is morpholine.

Compound (b), N-allyl-3-trimethylsilylpropiolic amide, one of the starting materials used to synthesize the fungicidal compound Formula (II) of the present invention, may be synthesized by various methods. Examples of the methods by which compound (b) may be synthesized are as follows:

SYNTHETIC METHOD 2

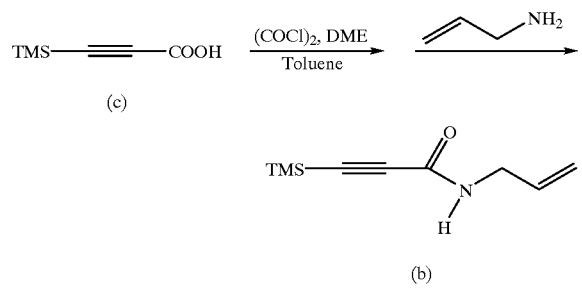

wherein TMS is trimethylsilyl, the chlorinating reagent is (COCl)$_2$ (oxalyl chloride), the catalyst is DMF (dimethylformamide) and the solvent is toluene.

The reaction is carried out by adding a catalytic amount of dimethylformamide to a solution of 3-trimethylsilylpropiolic acid in toluene. While the resulting mixture is agitated and maintained at a temperature of from about 2 to about 7° C., preferably about 5° C., oxalyl chloride is added dropwise over a period of 90 minutes to form an intermediate acid chloride. Examples of reagents which may be used to generate the intermediate acid chloride include the chlorinating reagents oxalyl chloride, phosphorous oxychloride and thionyl chloride, the catalyst DMF, and the optional solvents tetrahydrofuran and toluent. After the addition is complete, the reaction mixture is allowed to warm to room temperature and stir until the preparation of the intermediate acid chloride is complete. The excess oxalyl chloride is removed by distillation, and allyl amine is added dropwise over a period of about 10 minutes. The reaction temperature is maintained between about 10° C. and about 30° C. The reaction mixture is then extracted with water and the organic layer evaporated to yield the product, N-allyl-3-trimethylsilylpropiolic amide.

SYNTHETIC METHOD 3

-continued

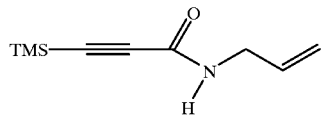

(b)

wherein TMS is trimethylsilyl, the base is n-BuLi (n-butyl lithium), and the solvent is THF (tetrahydrofuran).

The reaction is carried out by dissolving trimethylsilylacetylene in an solvent. Preferred solvents include ethereals such as THF, diethoxymethane and t-butylmethyl ether. At about 0° C., a strong base is added dropwise over a period of about 15 minutes. Examples of strong bases are n-butyl lithium and lithium diisopropyl amide. While still maintaining the temperature near 0° C., a solution of allyl isocyanate in solvent is added dropwise over about 15 minutes. This is followed by the dropwise addition of trimethylsilyl chloride. After holding the reaction mixture at about 0 to about 10° C. for about 3 hours, the reaction is quenched with aqueous ammonium chloride and extracted with dichloromethane. The solvent is evaporated to yield the product, N-allyl-3-trimethylsilylpropiolic amide.

SYNTHETIC METHOD 4

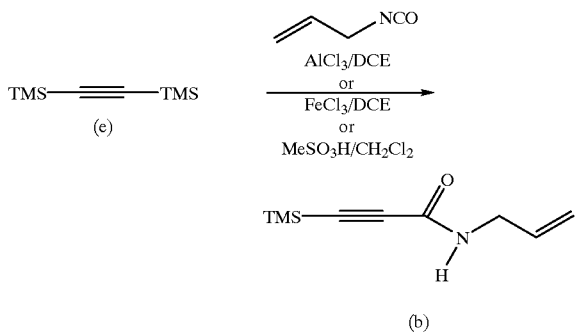

wherein TMS is trimethylsilyl, the solvents are methylene chloride or DCE (1,2-dichloroethane), and the acid catalysts are aluminum chloride ($AlCl_3$), ferric chloride ($FeCl_3$) or methanesulfonic acid ($MeSO_3$).

A solution of bis(trimethylsilyl)acetylene and allyl isocyanate in dry solvent is treated with an excess (at least 2 molar equivalents) of an acid catalyst. The preferred acid catalysts include aluminum chloride, ferric chloride and methanesulfonic acid; the most preferred acid catalyst is methanesulfonic acid. Acid catalysts which have been found not to work include: titanium tetrachloride, zinc chloride (in diethyl ether), Amberlyst 15 and Dowex 50 ion exchange resins, and gaseous hydrochloric acid in dioxane. 1,2-dichloroethane and o-dichlorobenzene are preferred solvents, the most preferred solvent is dichloromethane. The concentration of bis(trimethylsilyl) acetylene in the above reaction is preferred to be 1 molar or lower. The reaction is monitored by gas chromatography, and when product formation is complete the mixture is poured into water or saturated sodium bicarbonate and extracted with ethyl acetate. The organic phase is washed with water and brine, dried over sodium sulfate, filtered and evaporated to give an oil. When methanesulfonic acid is used as the catalyst, the oil may be used without further purification. When aluminum chloride is used as the catalyst, the oil is distilled under vacuum in a Kugelrohr apparatus (from about 100 to about 130° C. at from about 0.5 to about 1.0 Torr) to give the N-allyl-3-trimethylsilylpropiolic amide.

SYNTHETIC METHOD 5

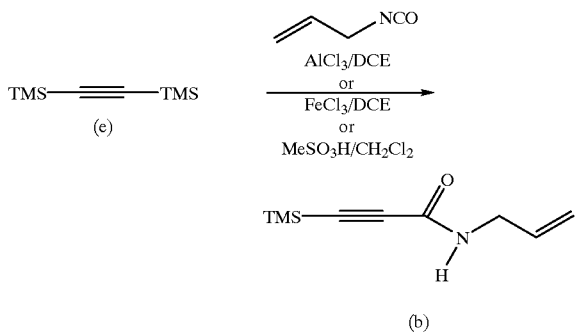

wherein TMS is trimethylsilyl.

The N-allyl-3-trimethylsilylpropiolic amide (b) may also be prepared by treating acetylene with a strong base such as n-butyl lithium or lithium diisopropylamide in an aprotic solvent such as tetrahydrofuran or diethoxymethane. The resulting lithium acetylide is treated with allyl isocyanate in situ to give N-allyl propiolic amide. Finally, treatment of the N-allyl propiolic amide with trimethylsilylchloride in the presence of a base provides N-allyl-3-trimethylsilylpropiolic amide.

The following examples illustrate some of these methods for synthesizing the compound of Formula (II). These examples are not meant to be limiting in any way.

Thin layer chromatography was used to monitor progress of the reactions and was carried out with varying concentrations of ethyl acetate/hexanes elutions. All reagents were purchased from Aldrich or Lancaster and used without purification.

EXAMPLE 1

Preparation of 4-hydroxy-4,5-dimethyl-2-trimethylsilanyl-dihydrothiophene-3-carboxylic acid allylamide (Formula (II)) from N-allyl-3-trimethylsilvlpropiolic amide (Compound (b))

TABLE 1

| Chemicals | Mol. Wt. | Total Weight | Total Volume | Total Moles |
|---|---|---|---|---|
| 3-mercapto-2-butanone | 104 | 3.5 g | 3.2 mL | 0.034 |
| Morpholine | 87 | 1.5 g | 1.5 mL | 0.017 |
| Diethoxymethane | 104 | 16.8 g | 20 mL | 0.16 |
| N-allyl-3-trimethylsilylpropiolic amide (b) | 181 | 3.04 g | — | 0.017 |

—not measured

A solution of 3-mercapto-2-butanone (2.1 g, 0.020 mol) and morpholine (1.5 g, 0.017 mol) in diethoxymethane (20 mL) was heated to reflux and treated with N-allyl-3-trimethylsilylpropiolic amide (3.04 g, 0.017 mol). The mixture is heated at reflux under a nitrogen atmosphere overnight. An additional portion of the 3-mercapto-2-butanone (0.7 g, 0.0067 mol) was added, and heating was continued for 4 hours more. A final portion of the 3-mercapto-2-butanone (0.7 g, 0.0067 mol) was added, heating was continued for 4 hours at reflux, then the mixture was cooled and evaporated under reduced pressure. The residue was extracted with two 40 mL portions of hot heptane, filtered, and allowed to cool (ice/salt bath). The resulting solid precipitate was collected by filtration and dried to give 4.0 g of 4-hydroxy-4,5-dimethyl-2-trimethylsilanyl-dihydrothiophene-3-carboxylic acid allylamide (84% yield).

EXAMPLE 2

Preparation of N-allyl-3-trimethylsilylpropiolic amide (Compound (b)) from 3-trimethylsilylpropiolic acid (Compound (c))

TABLE 2

| Chemicals | Mol. Wt. | Weight | Volume | Moles |
|---|---|---|---|---|
| 3-trimethylsilylpropiolic acid (c) | 142 | 28.4 g | (solid) | 0.2 |
| Toluene | 92 | 173 g | 200 mL | 1.88 |
| N,N-dimethylformamide | 73 | 0.2 g | 0.2 mL | 0.0027 |
| Oxalyl chloride | 127 | 28.4 g | 19.5 mL | 0.22 |
| Allyl amine | 57 | 25.7 g | 33.8 mL | 0.45 |

Dimethylformamide (200 mg, catalytic) was added to a solution of 28.4 g (0.2 mol) of 3-trimethylsilylpropiolic acid in toluene (200 mL). While the resulting mixture was agitated and maintained at a temperature of from about 2 to about 7° C., 28.4 g (0.22 mol) of oxalyl chloride was added dropwise over a period of 90 minutes to form an intermediate acid chloride. After the addition was complete, the reaction mixture was allowed to warm to room temperature and was stirred for about 6 hours, at which time gas chromatographic analysis showed that the preparation of the intermediate acid chloride was complete. The excess oxalyl chloride was removed by distillation, and allyl amine (25.7 g, 0.45 mol) was added dropwise over a period of 10 minutes. The reaction temperature was maintained between 10° and 30° C. The reaction mixture was then extracted with water (200 mL) and the organic layer evaporated to yield 28 g (77%) of a yellow-orange oil which was identified by $^1$H NMR and GC/MS (gas chromatographic/mass spectrographic analysis) to be N-allyl-3-trimethylsilylpropiolic amide.

EXAMPLE 3

Preparation of N-allyl-3-trimethylsilylpropiolic amide (Compound (b)) from trimethylsilylacetylene (Compound (d))

TABLE 3

| Chemicals | Mol. Wt. | Weight | Volume | Moles |
|---|---|---|---|---|
| Trimethylsilylacetylene (d) | 98 | 2.45 g | 3.5 mL | 0.025 |
| Tetrahydrofuran | 72 | 35.6 g | 40 mL | 0.49 |
| n-butyl lithium (1.6 M) | 64 | — | 17 mL | 0.027 |
| Allyl isocyanate | 83 | 2.1 g | 2.2 mL | 0.025 |
| Tetrahydrofuran | 72 | 8.9 g | 10 mL | 0.123 |
| Trimethylsilyl chloride | 108.5 | 2.7 g | 3.2 mL | 0.025 |
| Ammonium chloride solution | 53.5 | — | 75 mL | — |
| Dichloromethane | 85 | 265 g | 200 mL | 3.1 |

—not measured

Trimethylsilylacetylene (2.45 g (0.025 mol)) was dissolved in 40 mL of tetrahydrofuran. At 0° C., n-butyl lithium (17 mL, 1.6 M in hexane, 0.025 mol) was added dropwise over 15 minutes. While still maintaining the temperature near 0° C., a solution of 2.1 g (0.025 mol) of allyl isocyanate in tetrahydrofuran (10 mL) was added dropwise over 15 minutes. This addition was followed by the dropwise addition of 2.7 g (0.025 mol) of trimethylsilyl chloride (TMSCl). After holding the reaction mixture at about 0 to about 10° C. for about 3 hours, the reaction was quenched with 75 mL of aqueous ammonium chloride and extracted twice with 100 mL of dichloromethane. The dichloromethane is evaporated to yield 3.8 g of an oil which was purified by chromatography to yield 2.3 g (51%) of N-allyl-3-trimethylsilylpropiolic amide as identified by $^1$H NMR.

EXAMPLE 4

Preparation of N-allyl-3-trimethylsilylpropiolic amide (Compound (b)) from bis(trimethylsilyl) acetylene (Compound (e))

TABLE 4

| Chemicals | Mol. Wt. | Weight | Volume | Moles |
|---|---|---|---|---|
| bis(trimethylsilyl)acetylene(e) | 170 | 7.52 g | 10.0 mL | 0.044 |
| Allyl isocyanate | 83 | 3.76 g | 4.0 mL | 0.045 |
| Dichloromethane | 85 | 94 g | 50 mL | 0.78 |
| Methanesulfonic acid | 96 | 9.29 g | 6.3 mL | 0.097 |
| Ethyl acetate | 88 | — | — | — |
| Sodium bicarbonate | 84 | — | — | — |
| Sodium sulfate | 142 | — | — | — |

—not measured

A solution of bis(trimethylsilyl)acetylene (10.0 mL, 0.044 mol) and allyl isocyanate (4.0 mL, 0.045 mol) in dry dichloromethane is treated with an excess (at least 2 molar equivalents) of the acid catalyst methanesulfonic acid. The concentration bis(trimethylsilyl) acetylene was less than 1 molar. The reaction was monitored by gas chromatography, and when product formation was complete the mixture was poured into water or saturated sodium bicarbonate and extracted twice with ethyl acetate. The organic phase is washed with water and brine, dried over sodium sulfate, filtered and evaporated to give an oil.

EXAMPLE 5

Preparation of 4,5-dimethyl-N-2-propenyl-2-(trimethylsilyl)-3-thiophenecarboxamide (Formula (I))

from 4-hydroxy4,5-dimethyl-2-trimethylsilanyl-dihydrothiophene-3-carboxylic acid allylamide (Formula (II))

Formula (II) was synthesized according to Example 1. Formula (I) was then formed by dehydrating the compound of Formula (II) by dissolving the crude product of Formula (II) (1.06 g) in toluene and treating the solution with acetic anhydride (0.37 mL). The mixture was heated at 100° C. for 2 hours, then cooled, poured into saturated sodium bicarbonate and extracted with ethyl acetate. The organic phase was dried over sodium sulfate, filtered and evaporated. The residue was purified by chromatography over silica gel (2:1 hexane:ethyl acetate) to give 0.84 g of a yellow solid.

EXAMPLES 6 AND 7

Biological Assays

Formula (II), 4-hydroxy-4,5-dimethyl-2-trimethylsilanyl-dihydrothiophene-3-carboxylic acid allylamide, was tested for fungicidal effectiveness and has demonstrated control of Gg as shown in the following Examples.

EXAMPLE 6

In Vitro Assay

The test compounds (0.25 mL of an appropriate stock solution in acetone) were incorporated into 25 mL minimal media agar [prepared by autoclaving a solution of 17.5 g Czapek Dox broth (Difco), 7.5 g purified agar or Bacto-agar (Difco), and 500 mL distilled/deionized water, and then adding 50 $\mu$L of 1 mg/mL thioamine hydrochloride and 50 $\mu$L of 1 mg/mL biotin in 5% ethanol] and plates are prepared.

The compound of Formula (II) was tested on various isolates of *Gaeumannomyces graminis* (*Gg*) designated Isolates A-F. Each plate was inoculated by placing in a triangular shape three 4-mm plugs of *Gaeumannomyces graminis* (*Gg*) grown on the minimal media agar described above. The plates are incubated in the dark at 19 to 20° C. for 4 to 5 days. The growth of the fungus was measured as the diameter of the mycelial growth. The results were expressed as percent inhibition, calculated as [1-[(mm growth on treated plate—4)/(mm growth on control plate—4)]]×100.

TABLE 5

| | *Gaeumannomyces graminis* Inhibition (%) | | | | | | | | | | | | | | | | | |
|---|---|---|---|---|---|---|---|---|---|---|---|---|---|---|---|---|---|---|
| | Isolate A Test # | | | Isolate B Test # | | | Isolate C Test # | | | Isolate D Test # | | | Isolate E Test # | | | Isolate F Test # | | |
| Amount of Formula (II) (ppm) | 1 | 2 | 3 | 1 | 2 | 3 | 1 | 2 | 3 | 1 | 2 | 3 | 1 | 2 | 3 | 1 | 2 | 3 |
| 0.01 | 86 | 78 | 70 | 20 | 0 | −23 | 27 | 29 | 14 | 97 | 95 | 95 | 33 | 26 | 28 | 26 | 5 | 0 |
| 0.1 | 100 | 100 | 100 | 20 | −30 | −8 | 100 | 100 | 96 | 97 | 97 | 95 | 7 | 11 | 14 | 5 | 5 | 9 |
| 1.0 | 100 | 100 | 100 | 20 | 10 | 39 | 100 | 100 | 100 | 97 | 97 | 95 | 44 | 39 | 28 | 5 | 5 | 9 |
| 10.0 | 100 | 100 | 100 | 10 | 10 | 0 | 100 | 100 | 100 | 100 | 97 | 97 | 37 | 29 | 31 | 21 | 20 | 9 |
| 100.0 | 100 | 100 | 100 | 20 | 0 | 0 | 100 | 100 | 100 | 100 | 97 | 97 | 44 | 46 | 48 | 11 | 5 | 9 |

EXAMPLE 7

In Vivo Test 4 Week Seed Treatment Assay

Formula (II), 4-hydroxy4,5-dimethyl-2-trimethylsilanyl-dihydrothiophene-3-carboxylic acid allylamide, technical grade test material, assumed to be of nearly 100% purity, was weighed into small glass vials in the amounts of 12.5, 25, 50 and 100 mg. Each rate of technical material was dissolved in 2 mL acetone, and applied to 100 g "Ritmo" winter wheat. The untreated check of 100 g "Ritmo" also received 2 mL of acetone. The seed was treated by pouring the 100 g into the treatment bowl of a HEGE 11 seed treating machine, closing the lid, and starting the machine to spin the seeds. The solutions of technical material in acetone were slowly pipetted onto a spinning disk, which deposited the material onto the seeds. Treated seeds were allowed to spin for at least 15 seconds prior to collecting, and were placed in a paper sack and left to air dry for 24 hours prior to sowing.

"Conetainer" pots with approximately 120 mL capacity were filled from bottom to top with 20 mL wet vermiculite, 50 mL of *Gg*-infested soil, 3 seeds, and 15 mL of *Gg*-infested soil. A thin layer of vermiculite and a label describing the treatment information was added to each pot.

There were seven randomized repetitions for each treatment. The *Gg*-infested soil was prepared by mixing dried oat inoculum at a rate of 4% by volume to pasteurized soil. Dried oat inoculum was prepared by adding the fungus to twice-sterilized oat kernels, and allowing to incubate for approximately 30 days. Infested oats were then air-dried and stored in paper sacks at room temperature until use. After the 50 mL of infested soil was added to the cones, the soil in all cones was moistened. Three seeds of variety "Ritmo" were then added to each cone, and gloves were changed between each treatment. Seeds were covered with an additional 15 mL of infested soil and a thin layer of vermiculite. The cones were randomized and placed in a growth room with 18° C. day/15° C. night, 12 hour/12 hour light dark photo period, 16000 lux illumination, and 85% humidity. Cones were treated three times a week with 10 mL per cone. Emergence and vigor assessments were made one week after sowing.

After three weeks, the number of plants, severity of root rot, incidence of sclerotic lesions, and incidence of black culm were recorded for each conetainer. Disease assessments are defined as follows:

| Disease | Assessment |
|---|---|
| Root rot | Visual evaluation of the percentage of infected root area (%); |
| Sclerotic lesions | Incidence (%) of the plants exhibiting black, surface growth of the fungus on lower stems |
| Black culm | Incidence (%) of plants exhibiting total discoloration (internal fungus growth) of the stem |

The results of these tests are as follows:

TABLE 6

| | Root Rot | | | | |
|---|---|---|---|---|---|
| | Rate active ingredient | Disease Control Gaeumannomyces graminis (%) | | | |
| | | Isolate B | | Isolate A | |
| Active Ingredient | (g/100 kg seed) | Test 1 | Test 2 | Test 1 | Test 2 |
| Control | 0 | 0 | 0 | 0 | 0 |
| Formula (II) | 100 | 58 | 27 | 98 | 96 |
| Formula (II) | 50 | 20 | 15 | 87 | 97 |
| Formula (II) | 25 | −3 | 17 | 87 | 87 |
| Formula (II) | 12.5 | −4 | 15 | 76 | 84 |

TABLE 7

Sclerotic Lesions

| Active Ingredient | Rate active ingredient (g/100 kg seed) | Disease Control Gaeumannomyces graminis (%) | | | |
|---|---|---|---|---|---|
| | | Isolate B | | Isolate A | |
| | | Test 1 | Test 2 | Test 1 | Test 2 |
| Control | 0 | 0 | 0 | 0 | 0 |
| Formula (II) | 100 | 0 | 0 | 100 | 83 |
| Formula (II) | 50 | 0 | 0 | 100 | 83 |
| Formula (II) | 25 | 5 | 0 | 100 | 83 |
| Formula (II) | 12.5 | 0 | 0 | 100 | 75 |

TABLE 7

Black Culm

| Active Ingredient | Rate active ingredient (g/100 kg seed) | Disease Control Gaeumannomyces graminis (%) | | | |
|---|---|---|---|---|---|
| | | Isolate B | | Isolate A | |
| | | Test 1 | Test 2 | Test 1 | Test 2 |
| Control | 0 | 0 | 0 | 0 | 0 |
| Formula (II) | 100 | 0–12 | 42 | 100 | 100 |
| Formula (II) | 50 | −45 | 13 | 100 | 100 |
| Formula (II) | 25 | 0 | 13 | 100 | 100 |
| Formula (II) | 12.5 | 0 | 13 | 100 | 100 |

From the foregoing, it will be seen that this invention is unexpectedly found to control Gg and is one well adapted to attain all the ends and objects herein-above set forth together with advantages which are obvious and which are inherent to the invention.

It will be understood that certain features and subcombinations are of utility and may be employed without reference to other features and subcombinations. This is contemplated by and is within the scope of the claims.

Since many embodiments may be made of the invention without departing from the scope thereof, it is to be understood that all matter herein set forth is to be interpreted as illustrative and not a limiting sense.

What is claimed is:

1. A method of controlling disease in a plant caused by Gaeumannomyces sp. comprising applying a fungicidally effective amount of a fungicide of the formula (III)

or an agronomic salt thereof; wherein:
   Q is —NH, S, or O;
   W is O, or S;
   X is —H, —OAc, —OR, where R is lower alkyl;
   Y is S, O, or —NH;
   Z is —Si(R)$_3$, —C(R)$_3$, where R is lower alkyl;
   $R_1$ is a lower alkyl, allyl, or propargyl;
   $R_2$ is a lower alkyl or aryl; and
   $R_3$ and $R_4$ are independently chosen from hydrogen, a lower alkyl and aryl; and optionally, $R_2$ and $R_3$ together form a 5- or 6-membered carbocyclic ring.

2. The method of claim 1 in which the application is to a plant locus.
3. The method of claim 2 in which the application is to plant seed.
4. The method of claim 3 in which the application is to the soil.
5. The method of claim 1 where in Q is —NH.
6. The method of claim 1 wherein Q is S.
7. The method of claim 1 wherein Q is O.
8. The method of claim 1 wherein W is O.
9. The method of claim 1 wherein W is S.
10. The method of claim 1 wherein X is —OH.
11. The method of claim 1 wherein X is —Oac.
12. The method of claim 1 wherein X is —OR, wherein R is lower alkyl.
13. The method of claim 1 wherein Y is S.
14. The method of claim 1 wherein Y is O.
15. The method of claim 1 wherein Y is —NH.
16. The method of claim 1 wherein Z is —Si(R)$_3$.
17. The method of claim 1 wherein Z is —C(R)$_3$, where R is lower alkyl.
18. The method of claim 1 wherein $R_1$ is a lower alkyl.
19. The method of claim 1 wherein $R_1$ is allyl.
20. The method of claim 1 wherein $R_1$ is propargyl.
21. The method of claim 1 wherein $R_2$ is a lower alkyl.
22. The method of claim 1 wherein $R_2$ is aryl.
23. The method of claim 1 wherein $R_3$ is hydrogen.
24. The method of claim 1 wherein $R_3$ is a lower alkyl.
25. The method of claim 1 wherein $R_3$ is aryl.
26. The method of claim 1 wherein $R_4$ is hydrogen.
27. The method of claim 1 wherein $R_4$ is a lower alkyl.
28. The method of claim 1 wherein $R_4$ is a aryl.
29. The method of claim 1 wherein $R_2$ and $R_3$ form a 5-membered carbocyclic ring.
30. The method of claim 1 wherein $R_2$ and $R_3$ form a 6-membered carbocyclic ring.
31. The method of claim 10 wherein the fungicide has the formula:

(II)

32. A fungicidal composition comprising an agronomically acceptable carrier and a fungicidally effective amount of the compound (III)

or an agronomic salt thereof; wherein:
   Q is —NH, S, or O;
   W is O, or S;
   X is —OH, —OAc, —OR, where R is lower alkyl;
   Y is S, O, or —NH;
   Z is —Si(R)$_3$, —C(R)$_3$, where R is lower alkyl;
   $R_1$ is a lower alkyl, allyl, or propargyl;
   $R_2$ is a lower alkyl or aryl; and
   $R_3$ and $R_4$ are independently chosen from hydrogen, a lower alkyl and aryl;

optionally, $R_2$ and $R_3$ together form a 5- or 6-membered carbocyclic ring.

33. The composition of claim 32 in which the composition is a suspension concentrate.
34. The composition of claim 32 wherein Q is —NH.
35. The composition of claim 32 wherein Q is S.
36. The composition of claim 32 wherein Q is O.
37. The composition of claim 32 wherein W is O.
38. The composition of claim 32 wherein W is S.
39. The composition of claim 32 wherein X is —OH.
40. The composition of claim 32 wherein X is —Oac.
41. The composition of claim 32 wherein X is —OR, wherein R is lower alkyl.
42. The composition of claim 32 wherein Y is S.
43. The composition of claim 32 wherein Y is O.
44. The composition of claim 32 wherein Y is —NH.
45. The composition of claim 32 wherein Z is —Si(R)$_3$.
46. The composition of claim 32 wherein Z is —C(R)$_3$, where R is lower alkyl.
47. The composition of claim 32 wherein $R_1$ is a lower alkyl.
48. The composition of claim 32 wherein $R_1$ is allyl.
49. The composition of claim 32 wherein $R_1$ is propargyl.
50. The composition of claim 32 wherein $R_2$ is a lower alkyl.
51. The composition of claim 32 wherein $R_2$ is aryl.
52. The composition of claim 32 wherein $R_3$ is hydrogen.
53. The composition of claim 32 wherein $R_3$ is a lower alkyl.
54. The composition of claim 32 wherein $R_3$ is aryl.
55. The composition of claim 32 wherein $R_4$ is hydrogen.
56. The composition of claim 32 wherein $R_4$ is a lower alkyl.
57. The composition of claim 32 wherein $R_4$ is aryl.
58. The composition of claim 32 wherein $R_2$ and $R_3$ form a 5-membered carbocyclic ring.
59. The composition of claim 32 wherein $R_2$ and $R_3$ form a 6-membered carbocyclic ring.
60. The composition of claim 32 wherein the compound has the formula:

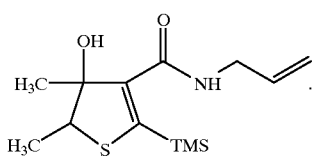

(II)

61. A compound having the structure:

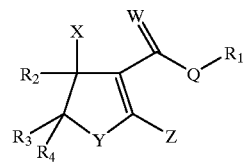

(III)

or an agronomic salt thereof; wherein:

Q is —NH, S, or O,

W is O, or S;

X is —OH, —OAc, —OR, where R is lower alkyl;

Y is S, O, or —NH;

Z is —Si(R)$_3$, —C(R)$_3$, where R is lower alkyl;

$R_1$ is a lower alkyl, allyl, or propargyl;

$R_2$ is a lower alkyl or aryl; and $R_3$ and $R_4$ are independently chosen from hydrogen, a lower alkyl and aryl;

optionally, $R_2$ and $R_3$ together form a 5- or 6-membered carbocyclic ring.

62. The compound of claim 61 wherein Q is —NH.
63. The compound of claim 61 wherein Q is S.
64. The compound of claim 61 wherein Q is O.
65. The compound of claim 61 wherein W is O.
66. The compound of claim 61 wherein W is S.
67. The compound of claim 61 wherein X is —OH.
68. The compound of claim 61 wherein X is —Oac.
69. The compound of claim 61 wherein X is —OR, wherein R is lower alkyl.
70. The compound of claim 61 wherein Y is S.
71. The compound of claim 61 wherein Y is O.
72. The compound of claim 61 wherein Y is —NH.
73. The compound of claim 61 wherein Z is —Si(R)$_3$.
74. The compound of claim 61 wherein Z is —C(R)$_3$, where R is lower alkyl.
75. The compound of claim 61 wherein $R_1$ is a lower alkyl.
76. The compound of claim 61 wherein $R_1$ is allyl.
77. The compound of claim 61 wherein $R_1$ is propargyl.
78. The compound of claim 61 wherein $R_2$ is lower alkyl.
79. The compound of claim 61 wherein $R_2$ is aryl.
80. The compound of claim 61 wherein $R_3$ is hydrogen.
81. The compound of claim 61 wherein $R_3$ is lower alkyl.
82. The compound of claim 61 wherein $R_3$ is aryl.
83. The compound of claim 61 wherein $R_4$ is a hydrogen.
84. The compound of claim 61 wherein $R_4$ is a lower alkyl.
85. The compound of claim 61 wherein $R_4$ is aryl.
86. The compound of claim 61 wherein $R_2$ and $R_3$ form a 5-membered carbocyclic ring.
87. The compound of claim 61 wherein $R_2$ and $R_3$ form a 6-membered carbocyclic ring.
88. The composition of claim 61 wherein the compound has the formula:

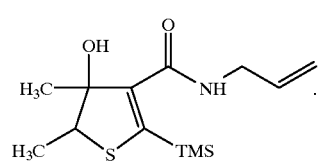

(II)

* * * * *

UNITED STATES PATENT AND TRADEMARK OFFICE
CERTIFICATE OF CORRECTION

PATENT NO.    : 6,291,513 B1                                      Page 1 of 1
DATED         : September 18, 2001
INVENTOR(S)   : Wendell G. Phillips et al.

It is certified that error appears in the above-identified patent and that said Letters Patent is hereby corrected as shown below:

<u>Column 13,</u>
Line 60, after "X is" replace "-H" with -- -OH --.

<u>Column 14,</u>
Line 33, after "is", delete "a".
Line 38, replace "10" with -- 1 --.

Signed and Sealed this

Twenty-first Day of January, 2003

JAMES E. ROGAN
*Director of the United States Patent and Trademark Office*